United States Patent
Padoy et al.

(10) Patent No.: US 10,311,178 B2
(45) Date of Patent: Jun. 4, 2019

(54) METHOD FOR ESTIMATING THE SPATIAL DISTRIBUTION OF THE HAZARDOUSNESS OF RADIATION DOSE FOR INDIVIDUALS SURROUNDED BY SOURCE(S) OF RADIATION

(71) Applicants: UNIVERSITE DE STRASBOURG, Strasbourg (FR); CENTRE NATIONAL DE LA RECHERCHE SCIENTIFIQUE—CNRS, Paris (FR); INSTITUT HOSPITALIER UNIVERSITAIRE DE STRASBOURG, Strasbourg (FR)

(72) Inventors: Nicolas Padoy, Strasbourg (FR); Nicolas Loy Rodas, Strasbourg (FR)

(73) Assignees: UNIVERSITE DE STRASBOURG, Strasbourg (FR); CENTRE NATIONAL DE LA RECHERCHE SCIENTIFIQUE—CNRS, Paris (FR); INSTITUT HOSPITALIER UNIVERSITAIRE DE STRASBOURG, Strasbourg (FR)

(*) Notice: Subject to any disclaimer, the term of this patent is extended or adjusted under 35 U.S.C. 154(b) by 6 days.

(21) Appl. No.: 15/501,319

(22) PCT Filed: Jul. 31, 2015

(86) PCT No.: PCT/EP2015/067639
§ 371 (c)(1),
(2) Date: Feb. 2, 2017

(87) PCT Pub. No.: WO2016/020278
PCT Pub. Date: Feb. 11, 2016

(65) Prior Publication Data
US 2017/0220716 A1  Aug. 3, 2017

(30) Foreign Application Priority Data

Aug. 4, 2014 (EP) .................................... 14306237

(51) Int. Cl.
G06F 17/50      (2006.01)
A61N 5/10       (2006.01)
G16H 50/50      (2018.01)

(52) U.S. Cl.
CPC ....... *G06F 17/5009* (2013.01); *A61N 5/1048* (2013.01); *A61N 5/1075* (2013.01); *A61N 2005/1094* (2013.01); *G16H 50/50* (2018.01)

(58) Field of Classification Search
CPC .......................... G06F 17/5009; A61N 5/1075
See application file for complete search history.

(56) References Cited

U.S. PATENT DOCUMENTS

| 5,077,685 A | 12/1991 | Iwashima et al. |
| 2012/0148131 A1 | 6/2012 | Couch et al. |

(Continued)

FOREIGN PATENT DOCUMENTS

| JP | 2000-152924 A | 6/2000 |
| JP | 2000-221292 A | 8/2000 |

(Continued)

*Primary Examiner* — Michael Jung
(74) *Attorney, Agent, or Firm* — Drinker Biddle & Reath LLP

(57) ABSTRACT

A method for estimating a spatial distribution of the hazardousness of radiation doses for individuals evolving in a medical operating room defining a three-dimensional environment surrounding at least one source of radiation. First a three-dimensional model of the environment is obtained. Then a simulation of radiation doses attributable to ionizing radiation emitted from the source and scattered by the environment is computed in the model. Then, an image indicating the spatial distribution of the hazardousness for an individual of the radiation doses is generated and displayed.

(Continued)

The three-dimensional model comprises models of individuals when the individuals are present in the environment and the image is a three-dimensional image generated for at least a portion of the model including said models of individuals.

14 Claims, 5 Drawing Sheets

(56) References Cited

U.S. PATENT DOCUMENTS

| | | | |
|---|---|---|---|
| 2013/0003915 A1 | 1/2013 | Lautenschlager et al. | |
| 2013/0048883 A1 | 2/2013 | Simon et al. | |
| 2014/0095117 A1* | 4/2014 | Vainshtain | G06F 17/5009 |
| | | | 703/1 |

FOREIGN PATENT DOCUMENTS

| | | |
|---|---|---|
| JP | 2004-065815 A | 3/2004 |
| WO | 2008/104915 A2 | 9/2009 |
| WO | 2014/052786 A2 | 4/2014 |
| WO | 2015/054314 A1 | 4/2015 |

* cited by examiner

METHOD FOR ESTIMATING THE SPATIAL DISTRIBUTION OF THE HAZARDOUSNESS OF RADIATION DOSE FOR INDIVIDUALS SURROUNDED BY SOURCE(S) OF RADIATION

CROSS-REFERENCE TO RELATED APPLICATIONS

This application is the U.S. national phase of the International Patent Application No. PCT/EP2015/067639 filed Jul. 31, 2015, which claims the benefit of European Application No. 14306237.0 filed Aug. 4, 2014, the entire content of which is incorporated herein by reference.

FIELD

The invention pertains to the field of signaling of the hazardousness of radiation doses in order to limit or prevent radiation exposure risks.

BACKGROUND

The use of radiation, such as ionizing radiation or electromagnetic fields, in applications requiring real-time minimally invasive imagery is becoming increasingly popular. In most applications, radiation used in imagery is used at levels and durations that minimize radiation exposure risks. In the field of surgical procedures, the patient is generally only exposed for a limited amount of time to potentially hazardous radiation doses. Nonetheless, clinicians are repeatedly exposed to a certain amount of potentially hazardous radiation doses which, over time, may lead to an increased risk of developing cancers or other health issues.

Typically, image-guided minimally invasive surgical procedures involve X-rays, Gamma-rays, the emission of radioactive particles or strong magnetic fields. Current surgical practice consists in using radioprotective equipment such as lead vests and aprons to minimize exposure. To measure the radiation dose accumulated over time by an individual, a single dosimeter is typically worn at chest level. Single dosimeters do not provide an accurate picture of the true radiation dose received by an individual. It is indeed well-established that human tissue responds differently to radiation depending on the area of the body that is exposed. To obtain a more accurate picture of the radiation exposure risk it would be necessary to wear a plurality of sensors such as dosimeters at different locations of the body, on the hands, head, torso and feet for instance, which is not convenient.

A more convenient approach consists in estimating the amount of radiation absorbed by individuals during procedures to increase staff awareness of radiation risk and influence their behavior in hazardous radiation environments.

Preliminary experiments conducted within the ORAMED project, aimed at establishing recommendations for clinicians and promoting radiation exposure awareness, have established that radiation scattered by the environment surrounding a source of ionizing radiation generates a more complex picture of radiation doses in an operating room than a simple direct propagation of the radiation from the source to the absorber.

Document EP 2 117 649 B1 provides a method of signaling the hazardousness of radiation doses emitted from a source of X-rays and scattered in a model of a surgical environment. The propagation of X-rays from the source and scattered by the modeled environment is simulated to determine radiation doses. The hazardousness of the radiation doses is displayed on the floor of the operating room, thus providing only a two-dimensional picture of the radiation hazard. Document EP 2 117 649 B1 thus fails to provide an accurate information to the individuals present in the operating room, mainly which parts of their bodies are exposed to the highest radiation exposure risk. Furthermore, EP 2 117 649 B1 simulates the propagation of X-rays in an operating room comprising still objects only, but fails to consider the impact of clinicians or staff present in the room and who also scatter the emitted X-ray radiation.

For the above reasons, a method of indicating the spatial distribution of the hazardousness of radiation doses attributable to a source of radiation is sought, that provides an accurate information as to which body parts are most concerned with radiation exposure risks and that can help increase the awareness of individuals of their radiation exposure during an intervention.

SUMMARY

To overcome the above-listed deficiencies of the prior art, the invention provides a method for estimating a spatial distribution of the hazardousness of radiation doses for individuals evolving in a medical operating room defining a three-dimensional environment surrounding at least one source of radiation, the method comprising:
  obtaining a three-dimensional model of the environment surrounding the source of radiation,
  computing, in at least a portion of said three-dimensional model, a simulation of radiation doses attributable to radiation emitted from the source of radiation and scattered by the environment;
  generating and displaying an image indicating the spatial distribution of the hazardousness for an individual of the radiation doses from the simulation.

The three-dimensional model comprises models of said individuals when said individuals are present in the three-dimensional environment; and the image is a three-dimensional image generated for at least a portion of the three-dimensional model including said models of individuals.

The invention overcomes the lack of precision of the prior art, by generating an image which represents the spatial distribution of the hazardousness of simulated radiation doses in three dimensions. Therefore, in the case of a surgical operation during which a source emits radiation, for example ionizing radiation such as X-rays, a clinician or other member of staff or another individual located near the source can look at the displayed image and identify which parts of his body are exposed to hazardous radiation doses. An individual can therefore react and adapt his position according to the information displayed so that none of his body parts, or none of his unprotected body parts such as for example the hands, limbs or head are exposed to hazardous radiation doses.

The invention overcomes another deficiency of the existing prior art in that the three-dimensional model that is obtained includes a model of any individual located in the three-dimensional environment surrounding the source of radiation. In the context of a surgical operation, any individual, in particular any individual evolving in the operating room, that is to say any individual other than the patient, is included in the model. The simulation of radiation doses that is computed in this model therefore becomes more accurate insofar as it includes the influence on the spatial distribution of radiation doses of the presence of individuals in the operating room. In particular, the invention more accurately computes the radiation doses absorbed and scattered by individuals.

The term "three-dimensional environment" refers to the space surrounding the source of radiation, and delimited by any solid object such as for example an operating table, instruments, tools, furniture, walls, ceiling, floor that scatters radiation. In the case of an operating room, the three-dimensional environment advantageously comprises all the solid objects of the operating room.

The term "three-dimensional model" refers to a virtual environment whose geometry matches that of the three-dimensional environment. The "three-dimensional model" may for example be a computer simulated reproduction of the three-dimensional environment. The three-dimensional model defines a space with boundaries at which radiation is scattered. The invention improves the methods of the prior art in that the three-dimensional model includes a modeled version of individuals present in the three-dimensional environment. The models of individuals also participate in the scattering of the radiation.

Advantageously, the method may further comprise: using a plurality of voxels in the three-dimensional model to map the environment.

The term "voxel" refers to a three-dimensional volume that may be cubical, parallelepiped, spherical. This volume defines an elemental volume of space corresponding to a portion of the air or an individual of the three-dimensional environment filled with a homogenous medium. It is possible to map the environment using such voxels.

By mapping the environment with voxels, it is possible to compute the radiation dose that is received at each voxel of the three-dimensional model so as to obtain a complete picture of the spatial distribution of the hazardousness of radiation doses in the three-dimensional environment. Notably, the size of voxels can be adjusted to fit precision criteria, and computation times. Voxels may for example not all have identical sizes in the three-dimensional model. The use of voxels may further simplify the step of computing a simulation of radiation doses insofar as a Monte Carlo type calculation may be used, for example one based on particle propagation and interaction algorithms.

According to an embodiment of the invention, the method may comprise: repeatedly updating the three-dimensional model to track movements in said environment.

By repeatedly updating the three-dimensional model, the invention may provide more reliable real-time information regarding the spatial distribution of the hazardousness of radiation doses. For example, by taking into account displacements of objects in an operating room, and updating the simulation of radiation doses, the invention may display up-to-date information that may allow individuals present in the operating room to see in real-time the evolution of the radiation exposure risk in the operating room.

According to an embodiment of the invention, the method may further comprise: recording radiation doses absorbed by voxels of a model of an individual.

The models of individuals may typically be made up of hundreds of voxels modeled for example as containing water, or a medium having the same properties as human tissue. These voxels can be tracked and the radiation dose that they are exposed to recorded, in order to provide a precise record of the radiation exposure, with information relating to which body parts were most exposed. This information can be used to later analyze the sequence of events during an operation and increase the awareness of clinicians or other individuals regarding which actions expose them to hazardous radiation, so that they may adapt their practice and reduce their radiation exposure.

Furthermore, the method may comprise: optimizing an arrangement of the environment based on a previously recorded radiation dose absorbed by voxels of the model of the individual.

The recorded radiation exposure of voxels of the model of an individual is information that may be correlated to specific environment arrangements, for example tool or machine arrangements. It may therefore be possible to identify arrangements that scatter radiations in inappropriate directions given the positions and movements of individuals in an operating room. Such recordings can further help optimize the positions and actions of individuals in an operating room as well as optimize the position of objects in the operating room.

Advantageously, the three-dimensional environment comprising radiation sensors, the method may further comprise a step of controlling radiation doses from the simulation using radiation doses measurements from the radiation sensors after obtaining the three-dimensional model and prior to computing a simulation of radiation doses.

The simulation of radiation doses may differ from the actual radiation dose perceived by an individual or sensor, for example in an operating room. This may for example be due to an incorrect assessment of the value of the radiation emitted by the source. By controlling the radiation doses from the simulation using radiation doses measured from sensors, it is possible to correct errors in the estimated radiation doses. Such an approach avoids false negatives and false positives when displaying a spatial distribution of the hazardousness of radiation doses.

According to an embodiment of the invention, it is possible to embed the three-dimensional image in a video stream of the environment to obtain an augmented reality image.

This embodiment may be particularly efficient at providing a realistic image in real-time to individuals surrounding the source of radiation. By seeing a video stream of themselves, for example on a screen, with an augmented reality image of the spatial distribution of the hazardousness of radiation doses, individuals can react quickly in case parts of their body are dangerously exposed. The image displayed may also issue a warning in case the hazard of the radiation doses exceeds a threshold value. An augmented reality view may thus contribute to increasing the radiation exposure awareness of individuals.

In an alternative embodiment, it is possible to overlay the three-dimensional image onto an image of the three-dimensional model.

This alternative way of representing the spatial distribution of the hazardousness of radiation doses can be more adapted for static representations, or for visualizing the simulated radiation doses on a screen prior to any human intervention. This representation may for example be used during test runs aimed at predicting radiation exposure risks and optimizing the arrangement of an environment such as an operating room.

Advantageously, the method may further comprise:
defining a color scale indicating the hazardousness of a radiation dose, and
representing each voxel in a color corresponding to the hazardousness of a radiation dose at said voxel in accordance with the color scale.

This way of generating the image of the spatial distribution of the hazardousness of the radiation doses is convenient. Indeed, the size of the voxels can be smaller in areas requiring a high resolution for example close to the radiation source, and bigger in areas less likely to require a high resolution, for example close to a ceiling.

In an alternative embodiment, it is possible to represent the hazardousness of the radiation doses in the form of isosurfaces.

By generating isosurfaces, it is possible to provide a more comprehensible image of the spatial distribution of the hazardousness of the radiation doses, particularly when this spatial distribution is complex.

According to an embodiment of the invention, the method may comprise:
  defining a bounding box centered on a model of an individual, said bounding box being smaller in size than the three-dimensional model, and
  performing the step of generating the image in the bounding box only.

By focusing the computational effort on areas surrounding individuals, it is possible to provide more accurate simulations of the spatial distribution of the hazardousness of radiation doses around individuals, for example by increasing the number of voxels used to map the portion of the three-dimensional environment corresponding to the volume of the bounding box. The use of bounding boxes may also contribute to making the generation of an image faster by reducing the amount of data points that need to be considered. By reducing the area in which the spatial distribution of the hazardousness of the radiation doses is represented, for example by limiting that area to bounding boxes, it is also possible to make the generated image more comprehensible, by displaying only the information that is most relevant for the individuals evolving in the operating room.

Advantageously, the method may comprise: repeatedly implementing the step of computing the simulation of radiation doses and generating and displaying the image when the source of radiation is active.

It may be particularly relevant to provide a real-time image of the spatial distribution of the hazardousness of radiation doses when the arrangement of the environment changes over time and when the source of radiation is active, or switched on. When the source is switched off, or inactive, predictive simulations may be computed that may not require real-time updates.

According to an embodiment of the invention, the source of radiation being switchable, the method may comprise:
  computing a simulation of expected radiation doses prior to switching on the source of radiation,
  blocking the switching on of the source of radiation when the image indicates that the expected radiation dose perceived by a model of an individual is hazardous.

By blocking the emission of radiation prior to switching the source of radiation on, it is possible to prevent an exposure of individuals to hazardous radiation doses. This embodiment may for example be implemented by comparing the total radiation dose already received by each individual present in the environment and block the switching on of the radiation source if this switching on would expose an individual to a radiation dose above a recommended threshold. The switching on may also be blocked if at least one body part of an individual is located in a region of the environment that would be exposed to a particularly hazardous radiation dose.

The invention also pertains to a system for indicating a spatial distribution of the hazardousness of radiation doses for individuals evolving in a medical operating room defining a three-dimensional environment surrounding at least one source of radiation, the system being adapted for:

obtaining a three-dimensional model of the environment surrounding the source of radiation, using signals from a plurality of cameras; and
  computing, in at least a portion of said three-dimensional model, a simulation of radiation doses attributable to radiation emitted from the source of radiation and scattered by the environment, and
  generating an image indicating the spatial distribution of the hazardousness for an individual of the radiation doses from the simulation; and
  displaying the image on a displaying device.

The system is adapted for obtaining models of individuals in said three-dimensional model when said individuals are present in the three-dimensional environment; and the system is also adapted for generating a three-dimensional image for at least a portion of the three-dimensional model including said models of individuals.

Such a system, for example in the form of a computer system, is suitable for implementing the method described above.

The invention also relates to a computer program product comprising program instructions, the computer program product being loadable into a data-processing device and adapted to cause the data-processing unit to carry out the steps described above when the computer program is run by the data-processing device.

Such a computer program product can also be defined as a non-transitory computer readable storage medium, having stored thereon a computer program comprising program instructions to implement the steps of the above-described method.

BRIEF DESCRIPTION OF THE DRAWINGS

The method of the invention will be better understood by reading the detailed description of exemplary embodiments presented below. These embodiments are illustrative and by no means limitative. They are provided with the appended figures and drawings on which.

For the sake of clarity, the dimensions of features represented on these figures and drawings may not necessarily correspond to the real-size proportions of the corresponding elements. Like reference numerals on the figures and drawings correspond to similar elements or items.

DETAILED DESCRIPTION

The invention provides a means of indicating on an accurate and comprehensible image an estimated spatial distribution of the hazardousness of radiation doses attributable to a source of radiation.

Although the method of the invention may be implemented in many different systems, in industrial facilities or natural environments containing sources of radiation, this description focuses on one application in the field of medical science, in which the source of radiation is a source of ionizing radiation, and more particularly X-rays.

Figure 1:
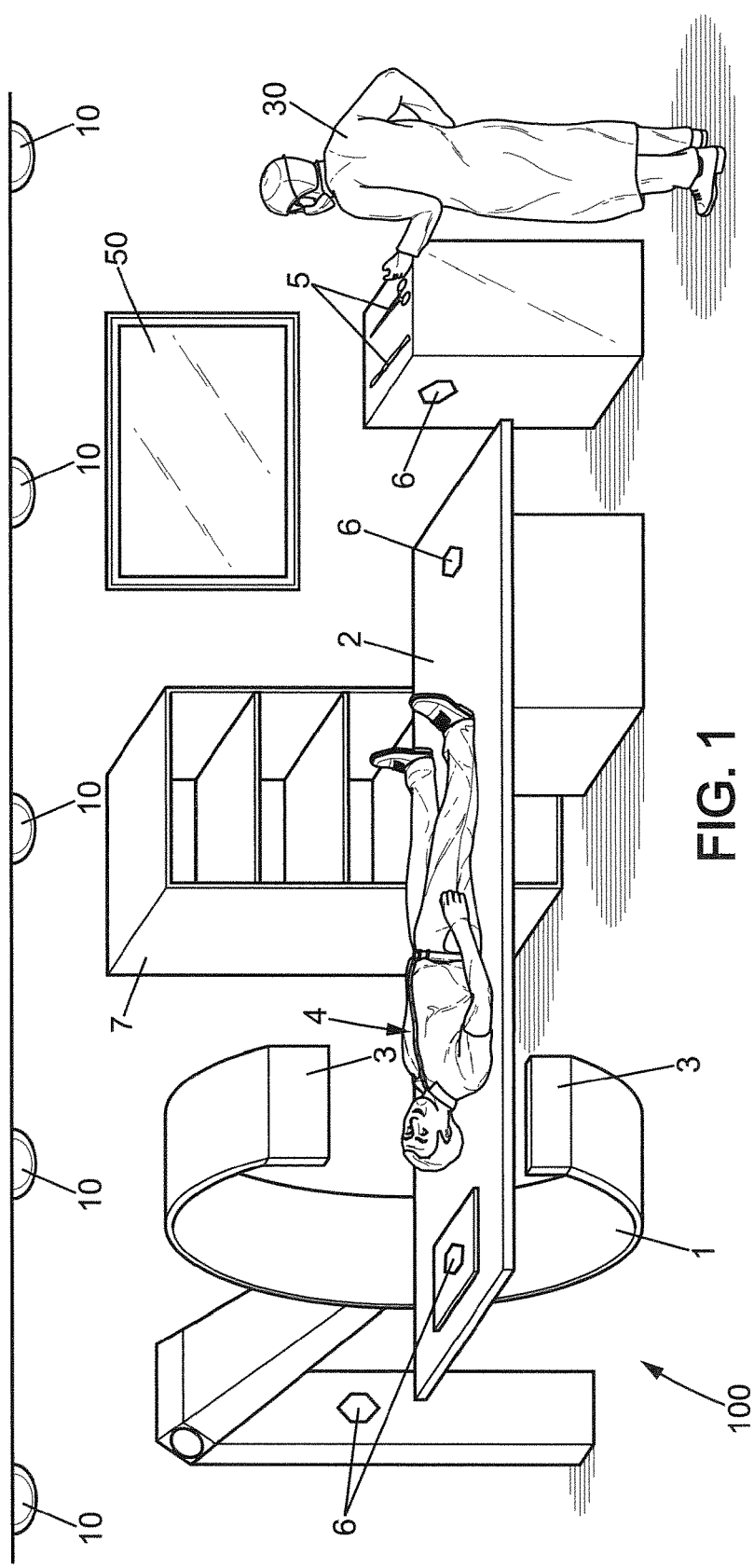
FIG. 1 is a schematic representation of a three-dimensional environment comprising a source of ionizing radiation.

As represented on FIG. 1, a three-dimensional environment 100 such as an operating room typically comprises an operation table 2, on which a patient 4 may be lying. The operating room may comprise other individuals 30 evolving in the operating room such as for example members of staff, clinicians or students. The three-dimensional environment 100 of FIG. 1 also comprises a medical device for performing imagery using X-rays. This device is represented as a C-arm 1, in which the sources of radiation 3 may be located at both extremities. The operating room may typically comprise furniture 7 such as for example medical apparatuses, and tools 5. On the ceiling of the three-dimensional environment 100, a set of cameras 10 may be used, for example an RGB-D system, where RGB stands for red, green, blue and D for depth, adapted for recording the three-dimensional environment 100 from different points of view to recreate a three-dimensional model such as that of FIG. 2. These cameras 10 may advantageously be positioned at strategic locations on the ceiling of the operating room.

The three-dimensional environment 100 of FIG. 1 also comprises a displaying device 50 such as a screen and sensors 6 sensitive to X-ray radiation, and capable of measuring the radiation dose that would be perceived by an individual at the location of each sensor. These sensors 6 may typically be configured to measure the Hp(10) radiation dose, corresponding to the dose that would be perceived 10 mm under the skin of a human being. Advantageously, these sensors 6 are wireless semiconductor dosimeters, capable of transmitting the measured dose in real time to a central processing unit.

When the source of X-rays 3 is active and emits X-rays, for example so as to provide a real-time scan of the patient 4, X-rays propagate through the three-dimensional environment 100 and scatter at objects of the operating room and at the patient. Any individual 30 evolving in the operating room also scatters X-rays, and receives a certain dose of X-ray radiation from direct emission from the source 3 as well as from radiation scattered by the three-dimensional environment 100. In the case, not represented on FIG. 1, of the presence of several individuals in the operating room, it may be particularly useful to take into account the influence of each individual on the spatial distribution of scattered X-ray radiation. As will be seen in relation to FIGS. 2 and 3, the invention does so and therefore provides an accurate estimation of the spatial distribution of the scattered X-rays, thereby providing reliable information on the spatial distribution of the X-ray radiation hazard in the operating room.

Figure 2:
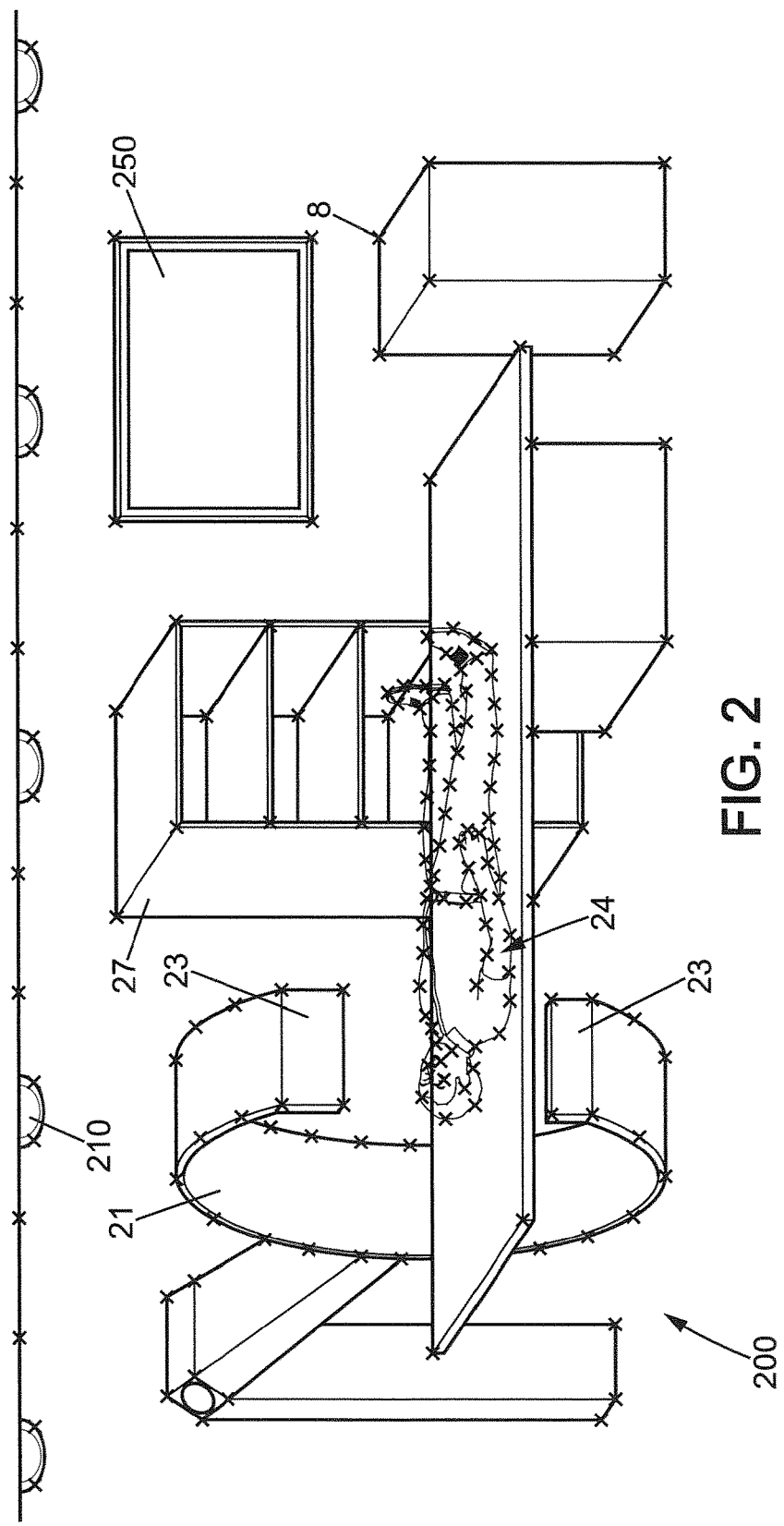
FIG. 2 is a schematic representation of a three-dimensional model of the environment of FIG. 1.
Figure 3:
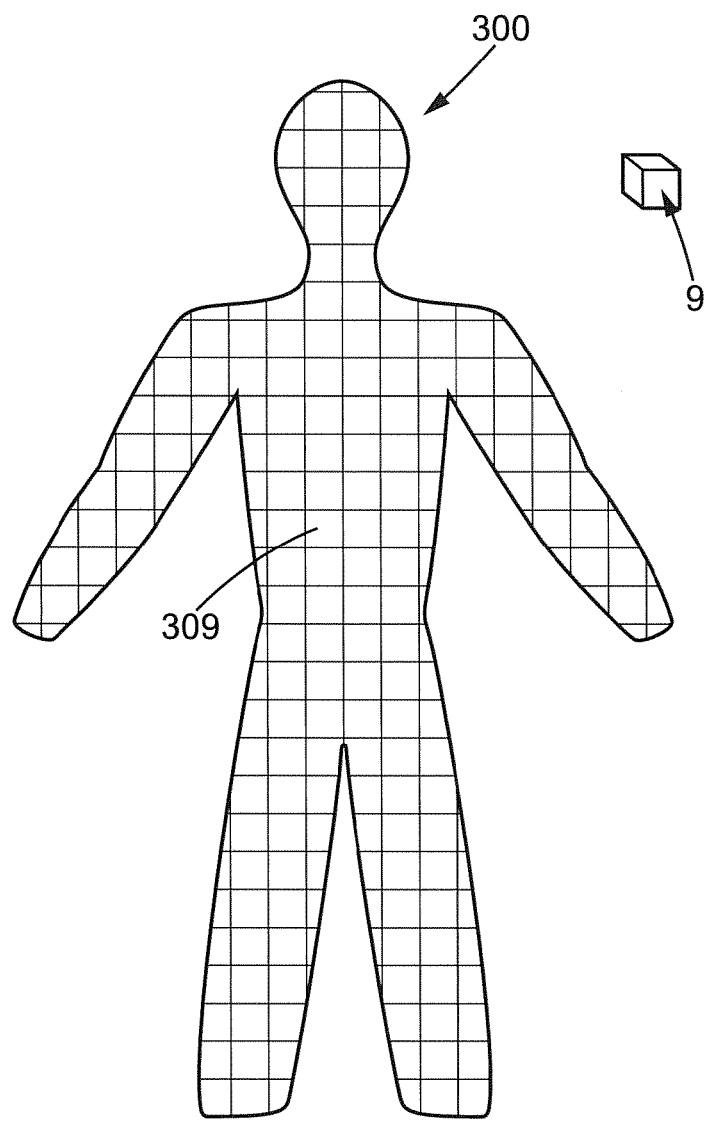
FIG. 3 is a schematic representation of a model of an individual with voxels.

The cameras 10 of FIG. 1 provide information that enables the generation of a three-dimensional model 200, represented on FIG. 2, of the three-dimensional environment 100. The three-dimensional model 200 appears as a set of objects the boundaries of which are defined by points 8, represented on FIG. 2 by Xs. To provide an accurate picture of these objects and their relative position in a three-dimensional space, the number of points 8 can be increased if deemed necessary. The model of the C-arm 21 and the model of the patient 24 may therefore comprise more points 8 than objects having a simpler geometry such as furniture 27, the screen 250 or cameras 210. Models of radiation sources 23 may also be included in this three-dimensional model 200.

Some tiny objects of the operating room such as tools 5 may be omitted in the three-dimensional model 200 to simplify the model and decrease computational time required to obtain the model. In addition to the elements described above, defining solid boundaries, individuals 30 evolving in the operating room and air can be included in the three-dimensional model 200 in the form of voxels 9 such as that represented on FIG. 3.

Voxels 9 may be three-dimensional volumes such as for example cubes, spheres or parallelepipeds defined all over the three-dimensional model 200 to fill the unoccupied volume of the three-dimensional model 200, which corresponds, in the three-dimensional environment, to the individuals evolving in the operating room and typically air. Each voxel corresponds to a specific medium, with specific physical properties such as for example radiation absorption coefficient, material type and scattering.

Voxels 9 may come in all sizes and shapes. It may for instance be particularly advantageous to map the volume of the three-dimensional model 200 with smaller voxels 9 in areas requiring a higher definition of the perceived radiation dose, such as on individuals, or in areas where the spatial distribution of the radiation doses is complex. It may on the other hand be advantageous to map the volume of the three-dimensional model 200 with bigger voxels 9 in areas located in regions that do not require a high definition or where the spatial distribution of the radiation doses is simple, such as for example close to the ceiling or far away from the radiation source in areas where individuals 30 are not likely to be present.

Individuals 30 evolving in the operating room are modeled as models 300 made up of voxels 309. The voxels of a model 300 of an individual can be tracked to keep a record of the radiation dose received by each voxel, thereby providing an accurate picture of the radiation dose received by a specific body part of an individual. By keeping a record of the radiation dose absorbed by the voxels 309 of the model of an individual 30 over time, the method of the invention provides information similar to that of an accurate dosimeter that can be used to identify which body parts were exposed to dangerous radiation doses. The method may also serve to issue warnings when a threshold radiation dose at a specific body part or over the whole body is exceeded on the model 300 of an individual 30.

The volume of the three-dimensional model 200 that is not occupied by a model 300 of an individual is assumed to be filled with air. To simulate human tissue in voxels 309 corresponding to a model 300 of an individual, it may for example be possible to associate a voxel 309 with a medium having a density of 1 g/cm$^3$ and a mass composition of 76.2% oxygen, 11.1% carbon, 10.1% hydrogen and 2.6% nitrogen. Voxels 9 corresponding to air may be associated with physical parameters typical for the composition of air.

Once the three-dimensional model 200 including the models 300 of individuals is obtained, the method of the invention comprises the step of computing a simulation of radiation doses in the obtained three-dimensional model 200 comprising models of individuals 300. The calculations are performed in each voxel by using Monte Carlo simulations. It may for example be convenient to use algorithms developed in particle physics such as those of the project Geant4, developed by CERN. Geant4 comprises code that can be used to compute the propagation of photons and their interaction with matter, taking into consideration such physical phenomena as, for example, Compton scattering, Rayleigh scattering, and the photoelectric effect.

The invention may adapt code available from the Geant4 project by providing numerical tools to compute a simulation of radiation doses in the voxels 9, 309 of the three-dimensional model 200. For example, the energy of the particles emitted by the radiation source 3 can be sampled from simulated X-ray spectra generated for selected peak voltages applied to the source, when the source is drivable with a voltage. Air Kerma values, Kerma standing for "kinetic energy released per unit mass", and filtrations may be computed using a X-ray Toolbox designed by Siemens. These tools, used in the three-dimensional model 200 defined above, allow a fast computation of radiation doses in the voxels 9, 309 of the three-dimensional model 200. A great number of particle trajectories can thus be computed, which protects the method from statistical errors.

Nevertheless, to further improve the accuracy of the simulated radiation doses, the method may use measurements from the wireless dosimeters 6 described above. These measure actual radiation doses at specific locations of the three-dimensional environment 100. These locations can be identified as corresponding voxels 9 in the three-dimensional model 200. In case of a difference between the computed simulation of radiation doses at these voxels 9 and the radiation doses measured by the wireless dosimeters 6 at these voxels, the radiation doses from the simulation may be controlled. For example, these simulated radiation doses may be calibrated using the measured values. A correction factor defined as the mean ratio between the measured and the simulated radiation doses can be computed and applied to the simulated radiation doses.

Figure 4:
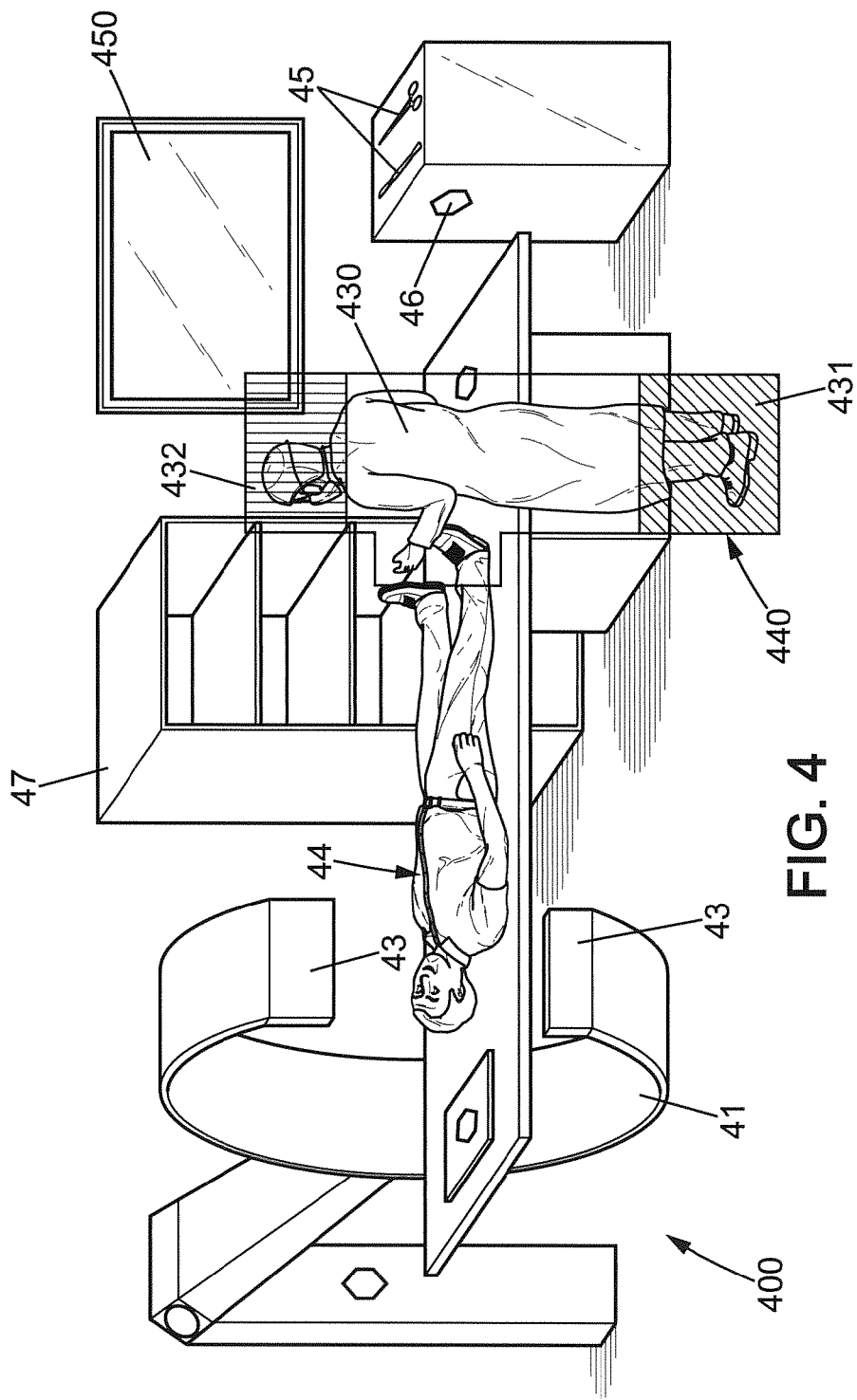
FIG. 4 is a schematic representation of an augmented reality image with bounding boxes surrounding an individual, displaying the spatial distribution of the hazardousness of radiation doses.

Once the value of radiation doses at each voxel 9 is computed, the method generates and displays an image of the spatial distribution of the hazardousness of these radiation doses, such as that represented on FIG. 4. The generation of the image 400 is based on the simulation performed in the step described above. FIG. 4 illustrates an augmented reality view of the image that was generated when implementing the method. This image comprises an image of an individual 430, an image of the C-arm 41, of the radiation sources 43, of the furniture 47 in the operating room, of the screen 450 on which image 400 may be displayed, of tools 45 and dosimeters 46. Although an augmented reality view such as that of FIG. 4 is particularly efficient at giving a sense of awareness of the radiation exposure risk to individuals who may look at image 400 on a screen, many alternatives to the representation of FIG. 4 may be used.

One convenient way of generating an image indicating the spatial distribution of the hazardousness of radiation doses may consist in defining a color scale for radiation doses, each color being associated with a level of hazardousness of the corresponding radiation dose. Then, each voxel 9, 309 may be filled with a color corresponding to the level of hazardousness of the radiation dose at that voxel.

An alternative way of generating the image 400 may consist in drawing isosurfaces corresponding to surfaces passing through voxels 9, 309 associated with the same value of radiation dose. If the spatial distribution of the radiation doses is complex, it may be possible to draw isosurfaces with voxels associated to similar values of radiation doses, that is to say values that differ by less than a predefined threshold. The purpose of such a representation is that it may be more comprehensible to look at, and may offer the additional advantage that it may be combined with volume rendering techniques to generate smoother images in which voxels 9, 309 are not seen. Indeed, voxels 9, 309 may appear as pixels on a screen, which may be disturbing to the eye.

These methods of generating the image may be implemented on an image of the three-dimensional model 200, or can be generated as an augmented reality image overlaid onto a video stream of the three-dimensional environment. FIG. 4 provides an illustration of the latter view.

According to a particularly advantageous embodiment of the invention, such as the one represented on FIG. 4, instead of generating an image representing the hazardousness of the radiation doses in all the voxels 9, 309 of the three-dimensional model 200, an image 400 may be generated for only a portion of that three-dimensional model 200. A particularly convenient representation consists in defining bounding boxes 440 around the model 300 of an individual and to display a corresponding bounding box 440 on the image 400 around the image of the individual 430. This bounding box may advantageously be centered on the image 430 of the individual. It may comprise different sections 431, 432, filled or simply shaded with colors or shades of grey in accordance with a scale associating a color or shade of grey to a particular value of radiation dose. On FIG. 4, the feet, head and torso of the image of the individual 430 represented on image 400, are each exposed to different radiation doses. The torso is not exposed to much radiation hazard, whereas the head and feet are. Image 400 from FIG. 4 displays this hazard in the form of shades of various densities in the corresponding sections 431, 432 of the bounding box 440.

The embodiment represented on FIG. 4 provides a comprehensive image of the radiation exposure risk. It can also be used to simplify the calculations when the simulations are performed with a higher resolution within the bounding boxes 440, and lower resolution outside of the bounding boxes 440. The resolution can for example be selected by choosing an appropriate size and number for the voxels 9, 309. By limiting the volume of the three-dimensional model 200 in which the step of generating an image is implemented, the method can be implemented quickly, and in real-time.

It is therefore easier to track the movements of individuals in the environment and repeatedly update the three-dimensional model 200 by tracking the movements of an individual 30, the change of position of the C-arm 1 and other objects 5, 7 manipulated by machines or individuals. All these movements may have an impact on the spatial distribution of the radiation doses and may require repeatedly implementing the step of obtaining a three-dimensional model 200, computing a simulation of radiation dose values in voxels 9, 309, and generating an image.

The augmented reality view of FIG. 4 can be displayed either on a screen, such as screen 50 of FIG. 1, or for example on wearable devices such as glasses using a virtual retinal display technology.

The method of the invention provides a more accurate information than prior art methods in that the model 300 of the individual is part of the three-dimensional model 200. Therefore, the influence of the model 300 of an individual is taken into consideration during the computing step, and the radiation absorbed and scattered by an individual 30 is included in the computed simulation. The information that is displayed may therefore be more accurate, especially in the presence of several individuals, each of whom absorbs and scatters part of the radiation doses emitted from the radiation source 3 and scattered by the environment.

Figure 5:
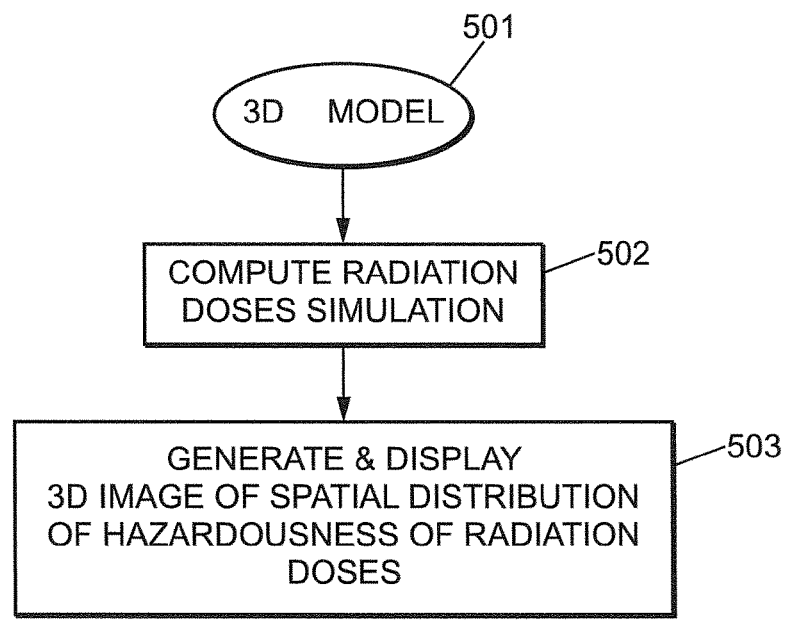
FIG. 5 is a flow chart showing three steps of the method of the invention.

FIG. 5 is a simplified flow-chart summarizing three steps of the method described above. First, a three-dimensional model 200 of a three-dimensional environment 100 is obtained at step 501. This model can be obtained by making a computer simulation with a computer system that generates a set of points 8 based on signals transmitted by RGB-D cameras 10 to provide a virtual copy of at least a portion of the three-dimensional environment 100. The portion that is selected is advantageously one in which an individual 30 is situated, potentially exposed to high values of radiation doses.

Then, a simulation of radiation doses is computed at step 502. This step may also be implemented by a computer system.

In step 503, a three-dimensional image of the spatial distribution of the hazardousness of radiation doses is generated, possibly with the help of the same computer system, and displayed, for example on a screen 50, or any other device.

Figure 6:
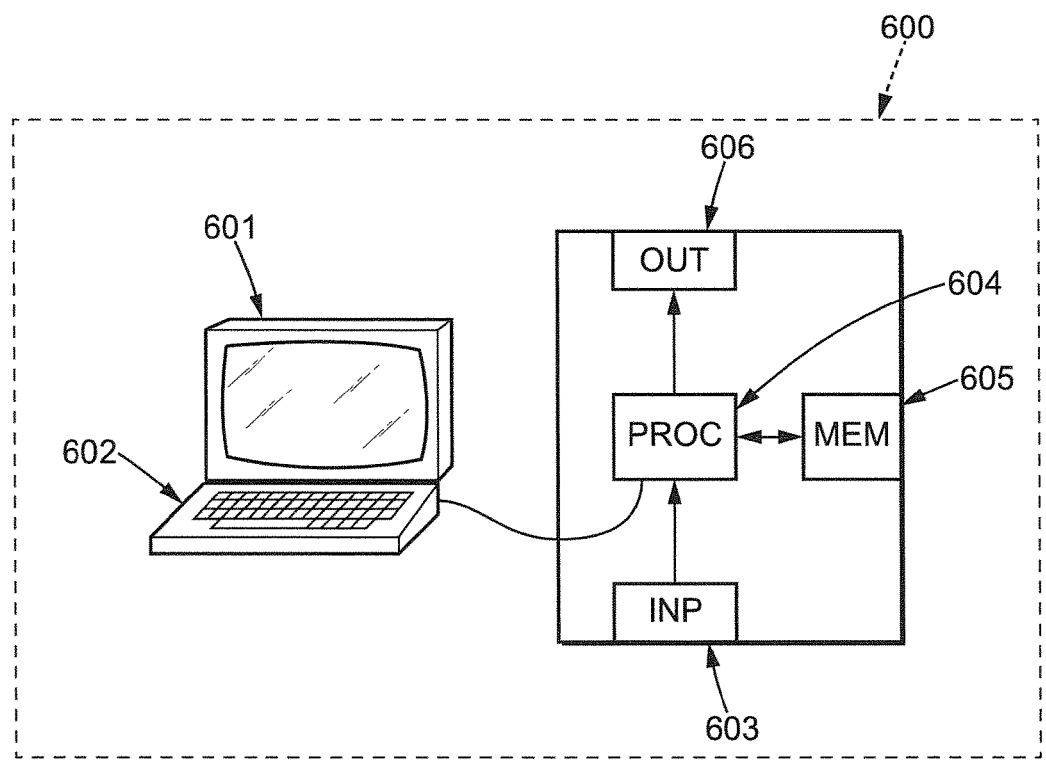
FIG. 6 is a possible embodiment for a computer system adapted for implementing the method invention.

FIG. 6 is a possible embodiment for a computer system configured for implementing the above-described method.

The computer system 600 comprises a computer, this computer comprising a memory 605 to store program instructions loadable into a circuit and adapted to cause circuit 604 to carry out the steps of the present invention when the program instructions are run by the circuit 604.

The memory 605 may also store data and useful information for carrying the steps of the present invention as described above.

The circuit 604 may be for instance:
- a processor or a processing unit adapted to interpret instructions in a computer language, the processor or the processing unit may comprise, may be associated with or be attached to a memory comprising the instructions, or
- the association of a processor/processing unit and a memory, the processor or the processing unit adapted to interpret instructions in a computer language, the memory comprising said instructions, or
- an electronic card wherein the steps of the invention are described within silicon, or
- a programmable electronic chip such as a FPGA chip (for <<Field-Programmable Gate Array>>).

This computer comprises an input interface 603 for the reception of data used for the above method according to the invention and an output interface 606 for providing a stacked model.

To ease the interaction with the computer, a screen 601 and a keyboard 602 may be provided and connected to the computer circuit 604.

The method described above provides an accurate, easily understandable estimation of the spatial distribution of the hazardousness of radiation doses on an image. The information displayed may be recorded, and analyzed to identify improvements that may be made in the arrangement of individuals and objects in the three-dimensional environment, and also increase the awareness of personnel or any individual towards the radiation exposure risks in the operating room.

For example, by watching the recorded evolution of the radiation exposure of a clinician during a surgical intervention, it is possible to identify clinical steps that expose specific body parts of the clinician to dangerous values of radiation doses. The clinician may be warned that he shall be more careful when performing such steps, and avoid certain areas of the operating room.

The method may also be used to identify safe locations in an operating room, and suggest these locations on an augmented reality image so as to minimize the radiation exposure risk. All this may be performed in real-time as well.

The method may further be used to optimize the arrangement of an operating room, so that the radiation preferentially scatters in directions that do not expose individuals to hazardous radiation doses. The method may therefore rely on previous recordings of a given type of surgical procedure, and dynamically optimize the arrangement of the C-arm 1 to reduce the scattered radiation to which an individual 30 such as a surgeon, clinician is exposed.

In another embodiment, it is possible to compute the spatial distribution of the hazardousness of radiation doses prior to switching on a source of radiation 3. If the switching on of the radiation source is estimated as being hazardous for individuals standing in the operating room, the method may send a warning message and/or may suggest safer positions for these individuals prior to authorizing the switching on of the source of radiation 3.

The method of the invention and the system implementing the method may also be used to send warning messages to individuals 30 that may be exposed to hazardous values of radiation doses. The warning may be sent when specific body parts requiring special care are exposed, such as the head. The warning may also be sent to an individual when the total radiation dose he has received exceeds a specific threshold value deemed to be hazardous.

The invention is not limited to the embodiments described above and may encompass equivalent embodiments.

For example, although the source of radiation may typically be a source of ionizing radiation, it may also be a source of any type of potentially hazardous electromagnetic radiation. For example, it may be possible to apply the method of the invention to estimate and display the spatial distribution of the hazardousness of strong magnetic fields, typically fields above 2 Tesla, that may be used in NMR imagery.

Furthermore, although the above description mentions that the patient 4 is typically considered as being a scattering object of the three-dimensional model 200 that is modeled by defining points 8 on his outer surface, the method may also model a patient with voxels in the same fashion as an individual 30 evolving in the three-dimensional environment. This may prove useful in determining the actual radiation doses to which the patient is exposed.

The invention claimed is:

1. A system for estimating a spatial distribution of the hazardousness of radiation doses for individuals evolving in a medical operating room defining a three-dimensional environment surrounding at least one source of radiation, comprising a plurality of cameras, the system being adapted for:
    obtaining a three-dimensional model of the three-dimensional environment surrounding the at least one source of radiation, using signals from the plurality of cameras, said three-dimensional model comprising models of said individuals when said individuals are present in the three-dimensional environment;
    computing, in at least a portion of said three-dimensional model, a simulation of radiation doses attributable to radiation emitted from the at least one source of radiation and scattered by the three-dimensional environment;
    generating an image indicating the spatial distribution of the hazardousness for an individual of the radiation doses from the simulation, the image being a three-dimensional image generated for at least a portion of the three-dimensional model including said models of individuals so that locations in the image of the models of the individuals respectively correspond in real-time to actual locations of said individuals in the three-dimensional environment;

displaying the image on a displaying device;

tracking movements in real-time of the individuals in the three dimensional environment using signals from the plurality of cameras; and repeatedly updating the three-dimensional model based on tracked movements of the individuals.

2. A non-transitory computer readable storage medium having stored thereon a computer program comprising program instructions, the computer program product being loadable into a data-processing unit and adapted to cause the data-processing unit to carry out a method for estimating a spatial distribution of the hazardousness of radiation doses for individuals evolving in a medical operating room defining a three-dimensional environment surrounding at least one source of radiation, the method comprising:

obtaining a three-dimensional model of the three-dimensional environment surrounding the at least one source of radiation, using signals from a plurality of cameras, said three-dimensional model comprising models of said individuals when said individuals are present in the three-dimensional environment;

computing, in at least a portion of said three-dimensional model, a simulation of radiation doses attributable to radiation emitted from the at least one source of radiation and scattered by the three-dimensional environment;

generating and displaying an image indicating the spatial distribution of the hazardousness for an individual of the radiation doses from the simulation, the image being a three-dimensional image generated for at least a portion of the three-dimensional model including said models of individuals so that locations in the image of the models of the individuals respectively correspond in real-time to actual locations of said individuals in the three-dimensional environment;

tracking movements in real-time of the individuals in the three dimensional environment using signals from the plurality of cameras; and repeatedly updating the three-dimensional model based on tracked movements of the individuals.

3. A method for estimating a spatial distribution of the hazardousness of radiation doses for individuals evolving in a medical operating room defining a three-dimensional environment surrounding at least one source of radiation, the method comprising:

obtaining a three-dimensional model of the three-dimensional environment surrounding the at least one source of radiation, using signals from a plurality of cameras, said three-dimensional model comprising models of said individuals when said individuals are present in the three-dimensional environment;

computing, in at least a portion of said three-dimensional model, a simulation of radiation doses attributable to radiation emitted from the at least one source of radiation and scattered by the three-dimensional environment;

generating and displaying an image indicating the spatial distribution of the hazardousness for an individual of the radiation doses from the simulation, the image being a three-dimensional image generated for at least a portion of the three-dimensional model including said models of individuals so that locations in the image of the models of the individuals respectively correspond in real-time to actual locations of said individuals in the three-dimensional environment;

tracking movements in real-time of the individuals in the three dimensional environment using signals from the plurality of cameras; and repeatedly updating the three-dimensional model based on tracked movements of the individuals.

4. The method of claim 3, further comprising: using a plurality of voxels in the three-dimensional model to map the three-dimensional environment.

5. The method of claim 4, further comprising:
defining a color scale indicating the hazardousness of radiation doses, and
representing each voxel in a color corresponding to the hazardousness of a radiation dose at said voxel in accordance with the color scale.

6. The method of claim 4, further comprising: recording radiation doses absorbed by voxels of a model of an individual.

7. The method of claim 6, further comprising: optimizing an arrangement of the three-dimensional environment based on a previously recorded radiation dose absorbed by voxels of the model of the individual.

8. The method of claim 3, the three-dimensional environment comprising radiation sensors, further comprising: controlling radiation doses from the simulation using radiation doses measurements from the radiation sensors after obtaining the three-dimensional model and prior to computing the simulation of radiation doses.

9. The method of claim 3, further comprising: embedding the three-dimensional image in a video stream of the three-dimensional environment to obtain an augmented reality image.

10. The method of claim 3, further comprising: overlaying the three-dimensional image onto an image of the three-dimensional model.

11. The method of claim 3, further comprising: representing the hazardousness of the radiation doses in the form of isosurfaces.

12. The method of claim 3, further comprising:
defining a bounding box centered on a model of an individual, said bounding box being smaller in size than the three-dimensional model, and
generating the image in the bounding box only.

13. The method of claim 3, further comprising: repeatedly computing the simulation of radiation doses and generating and displaying the image when the at least one source of radiation is active.

14. The method of claim 3, the at least one source of radiation being switchable, further comprising:
computing a simulation of expected radiation doses prior to switching on the at least one source of radiation,
blocking the switching on of the at least one source of radiation when the image indicates that the expected radiation dose perceived by a model of an individual is hazardous.

* * * * *